(12) United States Patent
Boffey

(10) Patent No.: US 10,857,398 B2
(45) Date of Patent: Dec. 8, 2020

(54) POWERED AIR PURIFYING RESPIRATOR

(71) Applicant: John Robert Boffey, Lutterworth (GB)

(72) Inventor: John Robert Boffey, Lutterworth (GB)

( * ) Notice: Subject to any disclaimer, the term of this patent is extended or adjusted under 35 U.S.C. 154(b) by 799 days.

(21) Appl. No.: 15/320,931

(22) PCT Filed: Jun. 30, 2015

(86) PCT No.: PCT/GB2015/051907
§ 371 (c)(1),
(2) Date: Dec. 21, 2016

(87) PCT Pub. No.: WO2016/001651
PCT Pub. Date: Jan. 7, 2016

(65) Prior Publication Data
US 2017/0136268 A1 May 18, 2017

(30) Foreign Application Priority Data

Jun. 30, 2014 (GB) .................................. 1411611.5
Aug. 6, 2014 (GB) .................................. 1413910.9

(51) Int. Cl.
| A62B 18/04 | (2006.01) |
| A62B 9/00 | (2006.01) |
| A62B 18/08 | (2006.01) |
| A62B 18/00 | (2006.01) |
| A61F 9/06 | (2006.01) |

(52) U.S. Cl.
CPC ............. *A62B 18/04* (2013.01); *A61F 9/065* (2013.01); *A61F 9/068* (2013.01); *A62B 9/006* (2013.01); *A62B 18/006* (2013.01); *A62B 18/08* (2013.01); *A61F 9/067* (2013.01)

(58) Field of Classification Search
CPC .. A61F 9/06; A61F 9/061; A61F 9/062; A61F 9/064; A61F 9/065; A61F 9/067; A61F 9/068; A62B 18/00; A62B 18/04; A62B 18/02; A62B 18/045; A62B 18/088; A62B 18/006; A62B 18/08; A62B 9/006;
(Continued)

(56) References Cited

U.S. PATENT DOCUMENTS 4,293,757 A * 10/1981 Niemi ..................... A61F 9/068
2/8.6
6,178,552 B1 * 1/2001 Robinson .................. A61F 9/06
2/8.1
(Continued)

FOREIGN PATENT DOCUMENTS

WO 2007019579 A2 2/2007
WO 2014091293 A1 6/2014

OTHER PUBLICATIONS

International Search Report dated Oct. 12, 2015.

*Primary Examiner* — Bradley H Philips
*Assistant Examiner* — Vincent D Hoang
(74) *Attorney, Agent, or Firm* — Wood, Phillips, Katz, Clark & Mortimer

(57) ABSTRACT

A personal powered air respirator, for example a welding or spraying helmet (10), includes a remote controller (30) for adjusting one or more operating parameters of the helmet and a means of displaying information regarding said parameter in, on or adjacent the interior of the vision panel (12) of the helmet. The invention allows for convenient adjustment in use. The remote controller is adapted to clothing, such as belt, glove or pocket, or may be incorporated in equipment for use with the helmet.

16 Claims, 3 Drawing Sheets

(58) Field of Classification Search
CPC ......... A62B 9/061; A62B 9/062; A62B 9/064; A62B 17/00; A62B 17/04; A61M 16/06; A61M 16/0683; A61M 16/0003; A61M 16/1005; A61M 2016/0061; A61M 2016/102; A61M 2210/1025; B23K 9/095; A41D 19/01529; A41D 19/01594; A41D 2600/202
USPC .................................. 128/201.25; 2/8.2, 8.6
See application file for complete search history.

(56) References Cited

U.S. PATENT DOCUMENTS

| | | | |
|---|---|---|---|
| 6,242,711 B1* | 6/2001 | Cooper | A61F 9/06 219/130.01 |
| 2007/0056073 A1* | 3/2007 | Martin | A61F 9/065 2/8.8 |
| 2008/0084390 A1* | 4/2008 | Jones | H04N 21/42206 345/158 |
| 2008/0189820 A1* | 8/2008 | Duffy | A61F 9/068 2/8.2 |
| 2010/0089887 A1* | 4/2010 | Friedl | B23K 37/006 219/130.21 |
| 2011/0219506 A1* | 9/2011 | Uttrachi | A61F 9/067 2/8.6 |
| 2013/0118487 A1* | 5/2013 | Huh | A61F 9/06 128/202.22 |
| 2014/0060538 A1* | 3/2014 | Volmer | A62B 7/10 128/204.21 |
| 2014/0166001 A1* | 6/2014 | Kooken | A62B 23/02 128/201.25 |

\* cited by examiner

POWERED AIR PURIFYING RESPIRATOR

CROSS-REFERENCE TO RELATED APPLICATIONS

This application is a National Stage application of Appin. No. PCT/GB2015/051907, filed Jun. 30, 2015, Great Britain Appin. No. 1411611.5, filed Jun. 30, 2014 and Great Britain Appin. No. 1413910.9, filed Aug. 6, 2014, the disclosures of which are hereby incorporated by reference in their entirety.

FIELD OF THE INVENTION

This invention relates to a powered air purifying respirator, and in particular to an air respirator under control of the user. The air purifying respirator may be self-contained and worn by the user, for example in the form of a backpack or belt pack.

BACKGROUND OF THE INVENTION

Air purifying respirators are worn during certain industrial and manufacturing processes to protect the user from dust, harmful gases and the like. The respirator generally comprises a mask or helmet which is maintained at positive pressure with respect to atmosphere, so that clean air is supplied for breathing and that any leakage is outward rather than inward.

The purified air supply may be from a pressurised tank via a pressure regulator, but may also comprise a fan unit whereby air is drawn in from atmosphere, and is filtered before being passed to the mask or helmet.

A particular instance of an air purifying respirator is used in welding, and comprises a helmet having an auto-darkening filter (ADF), which in turn comprises an electrically controlled lens adapted to switch from clear to dark as an electric welding arc is struck. Such lenses are well known and need not be further described here.

The air purifying respirator may be adjustable or controllable to vary parameters associated with use thereof, and in particular volumetric air flow. Such parameters may for example be set prior to use from an external control on the backpack.

In the case of a welding helmet, certain other parameters may be adjustable, in particular the delay or reaction time of the ADF. Again such parameters may be set prior to use from internal controls of the helmet, or may be pre-set.

Backpack mounted apparatus requires a power supply, typically rechargeable batteries or the like. The user must estimate or measure the remaining power so as to ensure that sufficient remains for the estimated time to complete the task. It may be particularly problematic should power fail part way through a complex welding procedure, because undesirable stresses and strains may be introduced if the weld is not completed within a specified time, such as when a weld is stopped and re-started; such interruption may cause the welded component to be scrapped, with consequent expense and delay.

It would be desirable to provide a device and method which addresses the factors noted above.

BRIEF SUMMARY OF THE INVENTION

According to a first aspect of the invention there is provided a personal powered air respirator comprising a helmet having a vision panel and for connection to a source of clean air and a power supply, said respirator further comprising a remote controller for adjusting an operating parameter of said respirator whereby information regarding said parameter is adapted to be displayed in, on, or adjacent the interior of said vision panel.

Such a controller permits adjustment of one or more operating parameters of the respirator whilst in use, and simultaneously displays the information relating to the parameter at the vision panel, so that the user can see the effect of adjustments. This arrangement is in contrast to a conventional controller, where a display is combined with adjustment controls in a single unit, and adjustment must consequently be made before donning the helmet. The arrangement is particularly advantageous where vision of the user is restricted, such as when wearing a welding helmet, and where the user's hands are in a protected environment, such as is provided by welding gloves or gauntlets.

In an embodiment of the invention, the remote controller also comprises a display, so that adjustments can be made when the helmet is not being worn, for example for test or certification purposes.

The remote controller may communicate with the helmet and other components of the respirator by cable, for example USB cable, or may use wireless communications using, for example BLUETOOTH™ protocol.

The remote controller is preferably adapted to an item of clothing or protective apparatus, such as a glove, belt, shield and/or pocket, or is adapted to a tool or appliance, such as a welding torch, spray gun, angle grinder, jack hammer or the like. Thus the remote controller may include a means of attachment to an item of clothing, such as a clip or fastener, or may be incorporated in the item of clothing. In the case of a tool, shield or appliance, the remote controller may be attached to, or part of the appliance, so as to be accessible for manipulation.

The vision panel of the helmet may comprise a display for information, or the information may be displayed in a portion or perimeter of a vision panel.

Information may comprise both an adjustable parameter and status information, such as air filter condition and/or remaining battery life. The information may further indicate operation of one of a plurality of control buttons or the like, so as to indicate to the user that the correct adjustment is being made or is about to be made. This arrangement may be useful in identifying a control button, such as one of "up" and "down" control buttons, when the hand of the user is gloved, or the user is not looking at the remote controller. It will however be understood that the remote controller is provided at a location suitable for manipulation.

In one embodiment the controller comprises a housing, for example of moulded plastic, external control buttons, and computer processor responsive to operation of such buttons to control or adjust parameters associated with the helmet, such as volumetric flow rate (fan speed). The housing may include means of attachment to a belt or glove, for example stirrups through which may be passed a belt, or any other kind of suitable fastener such as hook and loop material.

When glove mounted, the controller is typically mounted on the back so as not to impede movement of fingers within the glove, but to be operable by fingers of the other hand. On a tool, shield or appliance, the remote controller may be immediately adjacent a handle or other gripping feature.

The invention may be embodied in a welding helmet in which the vision panel is an ADF, and the controller is responsive to adjust parameters of the ADF, such as shade, delay or response time.

The source of clean air may be a backpack or belt pack mounted fan and filter or the like. The invention may comprise a helmet, fan/filter unit, and remote controller.

According to a second aspect of the invention, there is provided a method of adjusting an operating parameter of a helmet, for example a welding helmet, comprising:

providing a remote controller, providing a vision panel in said helmet, adjusting an operating parameter by manipulation of said remote controller, and providing in, on, or adjacent the interior of said vision panel, information concerning adjustments of said remote controller.

The method may further comprise display of information regarding a parameter of said helmet, and said information may be continuously displayed and/or displayed only upon adjustment of said parameter. Several kinds of information may be displayed simultaneously.

The method may further comprise providing an air quality monitor in said helmet whereby a parameter indicative of air quality is displayed in, on or adjacent said vision panel. Alternatively or additionally the method may include providing an alarm indicative of low air quality and triggered by said monitor.

BRIEF DESCRIPTION OF THE DRAWINGS

One feature of the invention will be apparent from the following description of an embodiment of the invention shown by way of example only in the accompanying drawings in which.

DETAILED DESCRIPTION OF THE INVENTION

Figure 1:
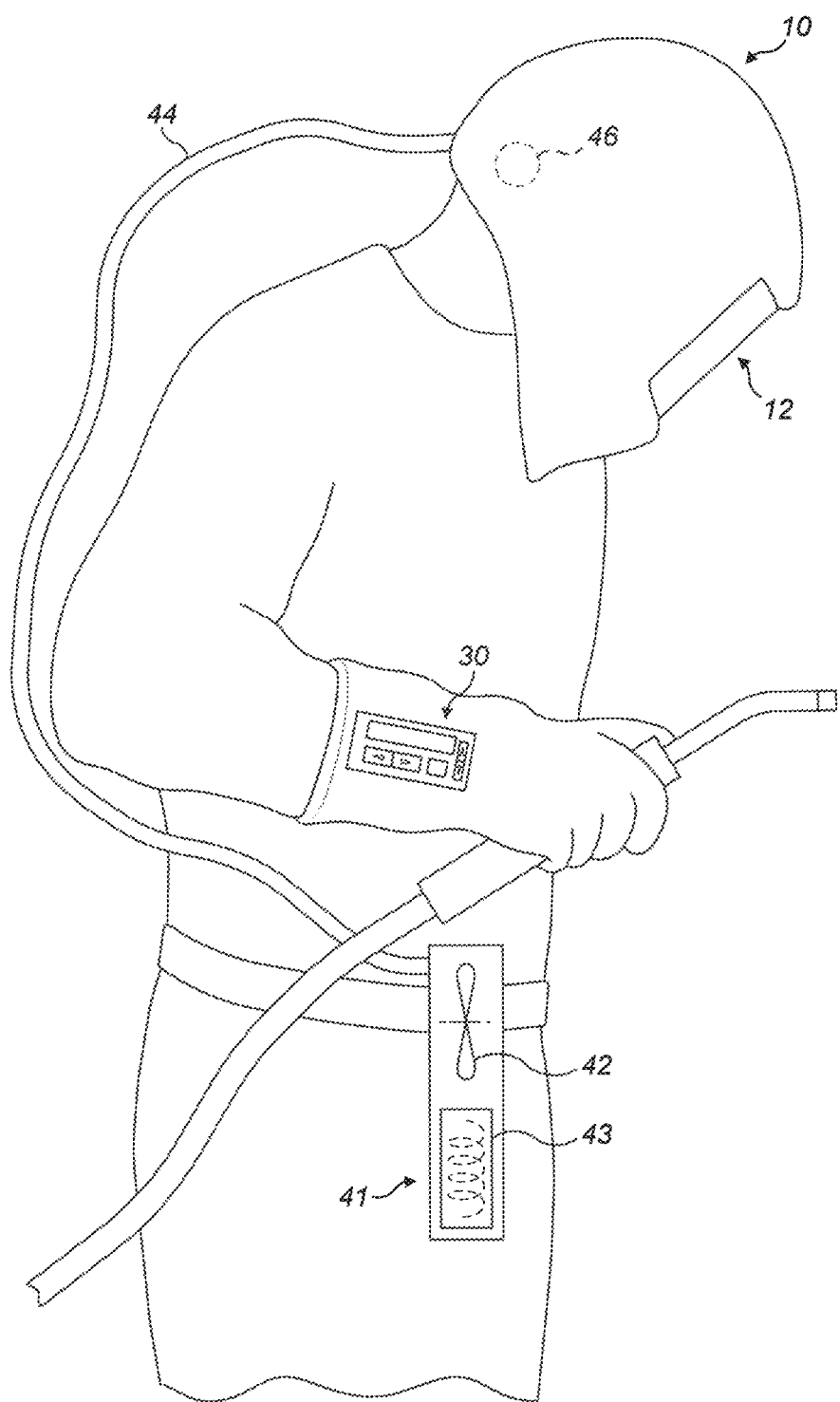
FIG. 1 shows a welder using a personal air respirator while welding according to the present invention.
Figure 2:
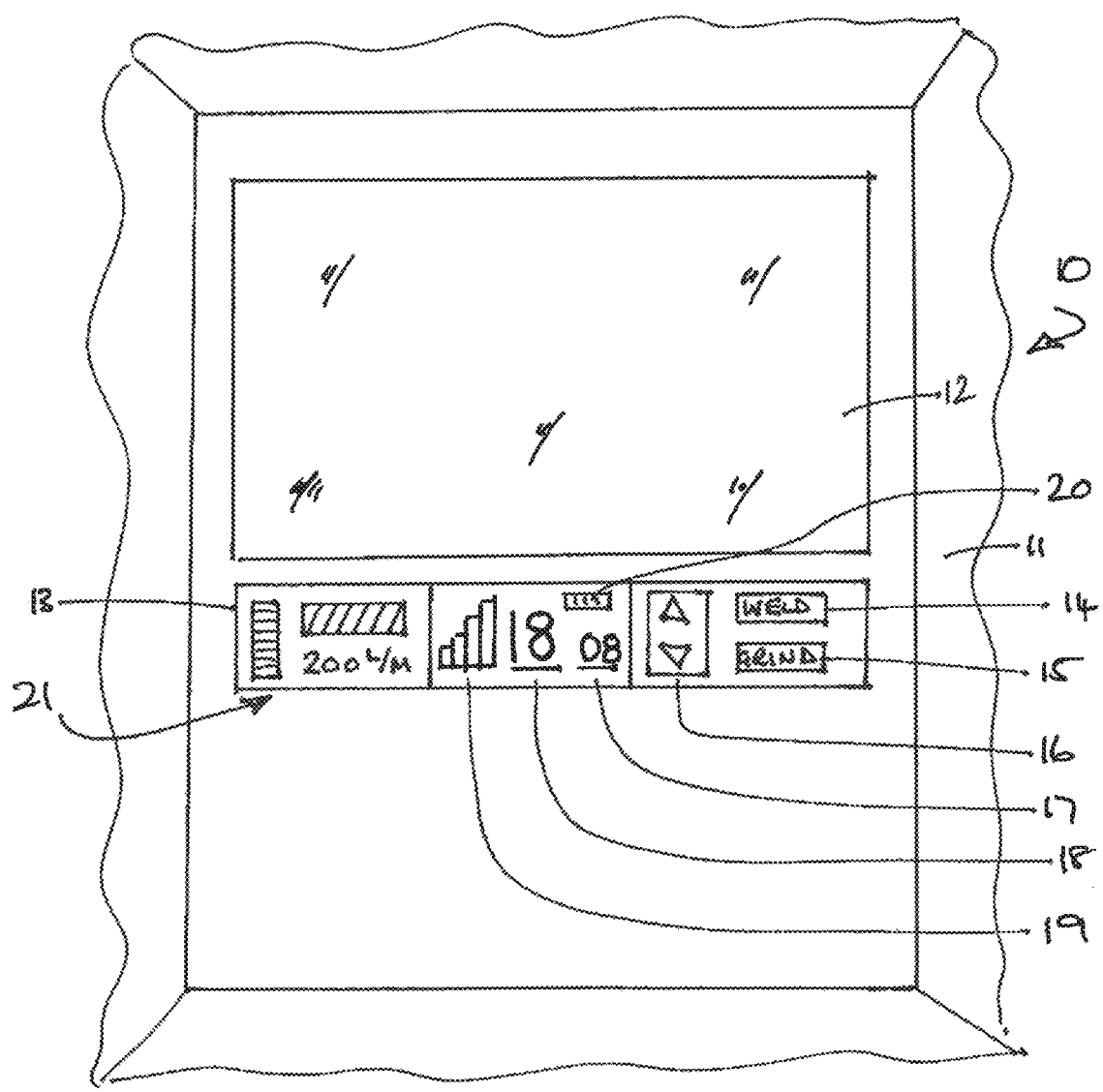
FIG. 2 is a schematic internal view of a welding helmet.
Figure 3:
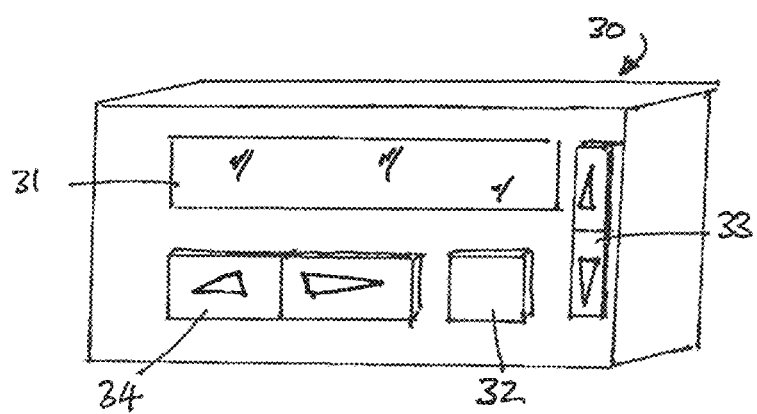
FIG. 3 is a schematic external view of a controller.

With reference to the drawings, a welding helmet 10 with an air supply comprises a housing 11 in which is provided an ADF vision panel 12.

Below the panel 12, and within the field of vision of the user, is a display 13. Any kind of information relating to the helmet may be displayed, of which the following are examples.

A status indicator 14,15 may indicate by illumination which of two or more alternative states are selected, in this case WELD or GRIND. The alternative states may automatically select certain respirator or ADF parameters.

A direction indicator 16 indicates the direction of adjustment, for example by illumination of the appropriate arrows.

A numerical indicator 17,18 may indicate the value of a parameter, for example an ADF response time or a volumetric air flow rate. Such a value may also be indicated by a graphical display, such as by illumination of sections of the progressive bar chart 19 or display of sections of a battery indicator 20.

Similar displays of function, selection, direction, value and amount may be provided for any parameter, and may include for example maximum, minimum, remainder, proportion and time. In the panel 21 is indicated two graphical and one numerical indication of volumetric air flow rate.

A controller 30, for example for belt or glove mounting comprises a display 31, an on/off button 32, and two up/down rocker switches 33,34 for adjustment of respirator parameters. The switches (which may comprises separate buttons) are orthogonally orientated to permit them to be distinguished without looking. Communication from the controller is by lead or more preferably is wireless, using for example BLUETOOTH™, to a body mounted respirator supply, which may comprise an adjustable speed fan and air filter supplying air under pressure to the helmet.

The controller is typically a microprocessor device having an internal power supply and memory.

Figure 4:
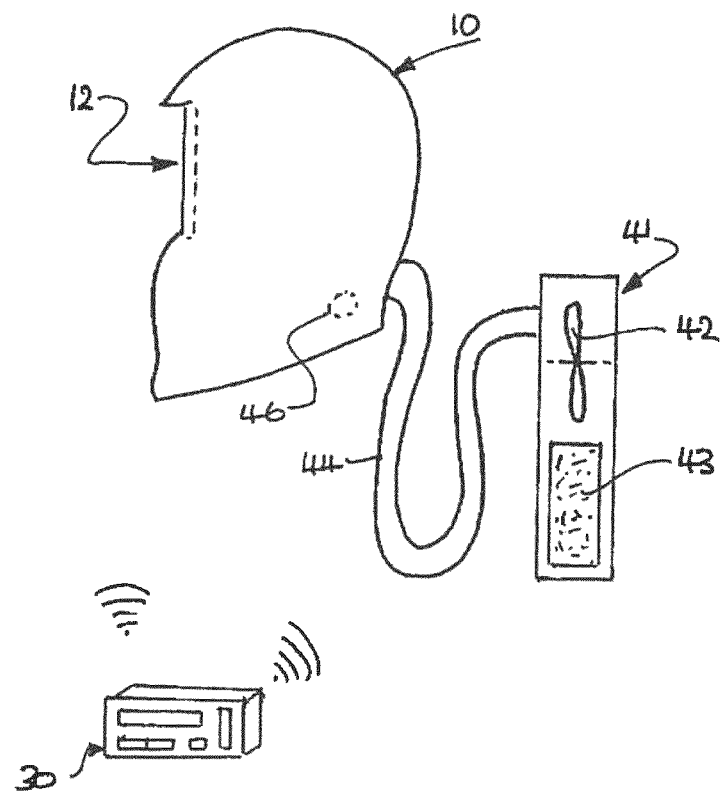
FIG. 4 is a schematic view of a helmet, air purifying unit and remote controller.

FIG. 4 illustrates schematically a respirator unit controlled by the remote controller 30, and comprising a backpack housing 41, a fan 42, a filter 43 for incoming air, and a hose 44 to direct outgoing air to a helmet 10. Such a respirator unit is worn on the body of the helmet user, and may further include a power supply, such as a rechargeable battery; such a battery may alternatively be separately provided in a belt pack or the like.

Connection of the controller 30, fan 42 and helmet 10 by electrical lead is envisaged, but for convenience it is anticipated that wireless communication will be preferred.

As noted above an air quality monitor or sensor 46 may be incorporated in the helmet, for example an oxygen deficiency sensor. The output of such a sensor may be used to display an air quality indicator in, on or adjacent the vision panel, and/or to trigger an alarm if air quality is low. The alarm may be visual and/or audible, and/or vibrating. The location of an audible or vibrating alarm may be in or on the housing 41, and communication between such an alarm and the monitor or sensor 46 may be by electrical lead or wirelessly.

An air quality monitor may be useful if, for example, welding gases enter the respirator unit. Indications relating to the monitor/sensor 46 may also be provided on the remote controller 30.

The physical size and shape of the controller 30 may be selected according to the intended use, to the number of parameters to be adjusted and to the difficulty of manipulation; for example oversize buttons may be provided where the user is expected to be gloved.

The invention claimed is:

1. A personal powered air respirator comprising a helmet having a vision panel, said helmet being for connection to a source of clean air and a power supply, said respirator further including a remote controller for adjusting an operating parameter of said respirator whereby information regarding said parameter is adapted to be displayed in, on or adjacent the interior of said vision panel, wherein the remote controller further comprises a housing, and the housing has a fastening means and wherein the remote controller is mounted on a glove by the fastening means.

2. A respirator according to claim 1 wherein said vision panel comprises an auto darkening filter for welding.

3. A respirator according to claim 2 wherein one of sensitivity and delay time of said auto darkening filter is adjustable from said remote controller.

4. A respirator according to claim 2 wherein the shade of said filter is adjustable from said remote controller.

5. A respirator according to claim 1 wherein said information is represented in one or more of alphabetical, numerical and diagrammatic form.

6. A respirator according to claim 1 wherein said remote controller includes a display for indicating the value of said parameter.

7. A respirator according to claim 1 wherein said remote controller communicates wirelessly with said vision panel.

8. A respirator according to claim 1 wherein said remote controller is adapted for attachment to clothing.

9. A respirator according to claim 1 wherein said remote controller is incorporated in a separate apparatus for use in conjunction with said respirator.

10. A respirator according to claim 9 wherein said apparatus is one of welding, grinding and spraying equipment.

11. A respirator according to claim 1 and further including an air quality sensor in said helmet.

12. A respirator according to claim 11 and further including an alarm responsive to said sensor for indicating low air quality.

13. A respirator according to claim 1 and further including a back-pack or belt-pack source of clean air connected to said helmet via a hose.

14. A respirator according to claim 13 wherein said source comprises a housing, a filter, a fan and a source of power for said fan.

15. A method of adjusting an operating parameter of a helmet having a supply of purified air, and comprising
    providing a remote controller wherein the remote controller further comprises a housing, wherein the housing has a fastening means and wherein the remote controller is mounted on a glove by the fastening mean,
    providing a vision panel in said helmet,
    adjusting an operating parameter of said helmet, by manipulation of said remote controller, and
    providing in, on or adjacent the interior of said vision panel information concerning adjustments of said remote controller.

16. A respirator according to claim 1 wherein the remote controller is mounted on the back of the glove.

\* \* \* \* \*